United States Patent
Wils et al.

(10) Patent No.: US 8,034,582 B2
(45) Date of Patent: Oct. 11, 2011

(54) PROCESS FOR CROSSLINKING PROTEINS WITH A KETOSE CONTAINING 3 TO 5 CARBON ATOMS

(75) Inventors: Daniel Wils, Morbecque (FR); Catherine Fouache, Sailly Labourse (FR)

(73) Assignee: Roquette Freres, Lestrem (FR)

( * ) Notice: Subject to any disclaimer, the term of this patent is extended or adjusted under 35 U.S.C. 154(b) by 529 days.

(21) Appl. No.: 11/012,485

(22) Filed: Dec. 16, 2004

(65) Prior Publication Data

US 2005/0130261 A1 Jun. 16, 2005

(30) Foreign Application Priority Data

Dec. 16, 2003 (FR) ...................... 03 14745

(51) Int. Cl.
- C12P 21/06 (2006.01)
- C12P 1/00 (2006.01)
- A23G 4/00 (2006.01)
- A23K 1/00 (2006.01)
- A61K 31/74 (2006.01)

(52) U.S. Cl. ............. 435/68.1; 435/41; 426/3; 426/615; 424/78.01

(58) Field of Classification Search ................. 435/68.1; 426/2, 630

See application file for complete search history.

(56) References Cited

U.S. PATENT DOCUMENTS

| | | | | |
|---|---|---|---|---|
| 4,351,835 A | * | 9/1982 | Stanko | 514/251 |
| 5,064,665 A | * | 11/1991 | Klopfenstein et al. | 426/2 |
| 5,561,110 A | * | 10/1996 | Michaelis et al. | 514/13 |
| 2003/0185960 A1 | * | 10/2003 | Augustin et al. | 426/602 |

OTHER PUBLICATIONS

Prabhakaram et al., Determination of Glycation Crosslinking by the Sugar-Dependent Incoproration of [14C]Lysine into Protein. 1994, Analytical Biochemistry, 216, 305-312.*

* cited by examiner

Primary Examiner — Ruth Davis
Assistant Examiner — Sheridan MacAuley
(74) Attorney, Agent, or Firm — Young & Thompson

(57) ABSTRACT

The present invention relates to a process for crosslinking proteins, according to which the crosslinking agent is a ketose containing 3 to 5 carbon atoms and said proteins are chosen from the group comprising proteins from animal tissues, from milk or from blood, such as in particular casein, gelatin or collagen; proteins from cereals, such as in particular maize, wheat or rice proteins; protein from high-protein plants, such as in particular pea, alfalfa, lupin, barley, millet or sorghum proteins; proteins from oleaginous plants, such as in particular soybean proteins, for instance soybean cakes, rapeseed or flax proteins, for instance rapeseed cakes, sunflower, groundnut or cotton proteins; and proteins from tubers, such as in particular from potato or manioc.

6 Claims, No Drawings

PROCESS FOR CROSSLINKING PROTEINS WITH A KETOSE CONTAINING 3 TO 5 CARBON ATOMS

FIELD OF THE INVENTION

The present invention relates to a process for crosslinking proteins, according to which the crosslinking agent is a ketose containing 3 to 5 carbon atoms.

The invention also relates to a process for crosslinking, with at least one ketose containing 3 to 5 carbon atoms, proteins intended for animal feed, for the production of film-forming compositions for coverings, coatings or adhesives, and for the preparation of biodegradable or renewable protein materials.

For the purpose of the invention, the expression "ketose containing 3 to 5 carbon atoms" is intended to mean a ketose chosen from the group consisting of dihydroxyacetone (or 1,3-dihydroxy-2-propanone), erythrulose, xylulose and ribulose.

The invention relates more particularly to the use of dihydroxyacetone for crosslinking proteins.

In addition, the expression "protein-crosslinking agents" or "protein-tanning agents" is intended to mean compounds capable of forming hydrogen bonds, coordinative bonds, covalent bonds or ionic bonds with said proteins in such a way as to reduce the digestibility and the water-solubility thereof.

BACKGROUND OF THE INVENTION

Three main families of protein-crosslinking agents are generally described.

The first family consists of mineral tannins, such as di-, tri- or polyvalent cation salts, for instance chromium, aluminium, iron, zinc, copper, cobalt, titanium, zirconium, silicon and caesium salts.

Mineral tannins are especially effective in alkaline medium. In their basic form, these polyvalent metal salts bond stably with the free carboxylic functions of certain amino acids of proteins.

Their field of application is in particular that of the tanning of biodegradable or renewable protein materials, in particular that of the production of leather by tanning the collagen constituting the dermis of the animal skin.

The aim of this operation is to convert the skin to leather, i.e. to convert a putrescible material into an imputrescible material, by taking away from the microorganisms the possibility of attacking the collagen fibres.

In the case of chromium tanning, which represents approximately 90% of the tanned hides in the world, the chromium compounds attach to the proteins by forming complexes:
  either with the free carboxylic groups of the amino chains of said proteins,
  or, by means of sulphate, formate or oxalate groups, with the free amine functions of the amino chains of said proteins.

Crosslinking, i.e. bonding of two or more peptide chains, by means of the chromium compounds, then occurs.

These mineral tannins are particularly effective but generate large amounts of waste that are prejudicial to the environment.

Mineral tannins are sometimes also used in the field of tanning proteins intended for animal feed, in the form of zinc salts or salts of other cations. Excessive consumption of such tanned proteins is to be avoided since it can result in toxic effects for the animal.

The second family of tannins consists of synthetic tannins such as epichlorohydrin resins, polyamide-amine-epichlorohydrin resins, polyethyleneimine resins and isocyanate resins such as methylenediphenyl diisocyanate.

Their field of application is in particular that of glues or adhesives, in particular wood glues or glues for corrugated cardboard.

The third family of tannins consists of aldehyde tannins, more particularly formaldehyde, glyoxal (ethanedial) or glutaraldehyde, and all the commercial derivatives thereof sold in the form of various condensates.

Aldehyde tannins bond to proteins via covalent bonds, mainly generating condensation products. A double condensation reaction may also result in the formation of crosslinked products.

These condensation products are generally derived from the reaction forming imines by condensation of the carbonyl function of the crosslinking agent with the free amine function of certain amino acids of said protein (in particular the $\epsilon$-amino function of lysine).

Aldehyde tannins are in particular used in three main fields of application.

The first field of application is that of the preparation of protein materials, for example leathers, moulded items, textile fibres, pharmaceutical or food capsules, photographic films, motor car parts and buttons, from milk caseins, zeins, collagens, soybean proteins, blood from an abattoir, and gelatins, most commonly crosslinked with formaldehyde.

For leathers, the tanning with aldehyde agents consolidates the structure of the collagen by creating bonds between groups of the aldehyde tannin and at least two groups belonging to the peptide chain. Specific leathers can thus be obtained.

The second field of application is that of the tanning of proteins intended for the production of film-forming compositions for coverings, coatings or adhesives.

Use is commonly made, for example, for bonding papers, cardboards, particles, wood or other materials, of adhesives prepared from gelatin, from blood proteins, from fish proteins, from milk caseins or from plant proteins, to which formaldehyde or glyoxal is generally added in order to improve the water- and moisture-resistance of the adhesive joint and also its adhesive characteristics.

The third field of application is that of the tanning of proteins intended for feed, in particular ruminant feed, for producing "resistant" proteins.

The resistant proteins are then proteins that have been modified in such a way that they are less degraded by certain microbial enzymes in the rumen.

However, after having passed through the rumen, these proteins once again have satisfactory digestibility when they arrive in the rennet stomach and in the small intestine. The acid pH and the digestive enzymes in fact free the proteins and thus make them available again.

This tanning operation therefore allows better assimilation of the food intake by ruminants, resulting in better zootechnical performance levels (improved meat and milk productions).

However, the major drawback of the aldehyde tannins used in these three fields of application is their high toxicity.

One of the aldehydes most commonly used, because it is very reactive, is formaldehyde (also referred to as formol under its common technical name). Now, this chemical agent is among the most toxic and the most dangerous of the aldehyde tannins to handle, since it is in the gaseous state at ambient temperature.

In the field of ruminant feed, in order to remedy this use of substances that are active but too toxic, it has been proposed, for example in patent EP 284,548, to perform a tanning reaction by means of a particular category of aldehydes, e.g. aldoses.

These are xylose, ribose, mannose, lactose and glucose. These molecules are non-toxic, unlike the aldehyde tannins conventionally used.

However, the teaching of that patent reveals that it is necessary to finely control the tanning reaction so as to obtain what the authors of that patent call an "early" Maillard condensation product rather than an "intermediate" Maillard product.

It is also essential to select a food described as "orthodox", i.e. containing a group of proteins with a free amine function present in the food in a ratio of 1.5 to 1 relative to the total proteins.

Finally, it is necessary to hydrolyse the condensation product at a pH of less than 4, and to limit the percentage of reducing sugars therein.

The process described in patent EP 284,548 is therefore much too laborious to carry out.

Besides the aldoses proposed in patent EP 284,548, a single ketose is mentioned in said patent application. This is fructose.

However, this ketose containing 6 carbon atoms is only considered because of its intermediate reducing capacity between those of glucose and mannose. That patent EP 284,548 merely cites this ketose without truly recommending it. No other ketose is used in the process described.

Moreover, to the applicant company's best knowledge, the potentialities and the chemical reactivities of other sugars carrying a ketone function have never been the subject of an examination with respect to the fields of activity with which the present invention is concerned.

The simplest ketose of the sugar series is dihydroxy-acetone (or DHA), also called 1,3-dihydroxy-2-propanone, which is a compound of formula $CH_2OH—CO—CH_2OH$.

Besides its use in the cosmetics sector, but in external applications for its properties of colouring the epidermis of the skin ("self-bronzing" effect)—used alone or combined with erythrulose—DHA is especially known for its antioxidant, odour-inhibiting and biocidal properties (antibacterial effect and antibacterial and antifungal effects).

DHA is especially recommended as a mixture with pyruvic acid, in particular for ensuring metabolic control of the lipid content of the liver and of adipocytes. It is then possible to control, by this means, the lipid/protein balance in mammals.

This use is, for example, described in U.S. Pat. No. 4,351,835, by oral administration of pyruvate and of DHA in order to avoid weight gain in mammals, or in U.S. Pat. No. 4,415,575, where the administration thereof promotes protein concentration in animals:

In order to illustrate another known property of DHA, i.e. its inhibitory effect on undesirable odours, patent application JP 50,7803 describes the use of DHA in preventing the resurgence of odours from oils or from fats.

The biocidal effect of DHA is, for its part, described, for example, in patent CA 1,054,434. It is used as a food additive, in particular for preserving foods (fish, meat, fruit, vegetables, etc.), by bringing the food into contact with DHA at ambient temperature.

As regards ketoses containing 4 or 5 carbon atoms (i.e. erythrulose, ribulose or xylulose), unlike DHA, they do not appear, according to the literature, to have been the subject of work studies on their intrinsic properties.

The latter molecules are, to the applicant company's knowledge, only used today as synthesis intermediates of products with added value, such as their corresponding hydrogenation products (erythritol, ribitol, arabitol and xylitol).

From all the above, it results that there is an unsatisfied need for having a substitute for crosslinking agents, in particular a substitute for mineral tannins, for synthetic tannins and for aldehyde tannins, that is simple to produce and to use and that is of equivalent, or even improved, effectiveness compared with the conventional tanning agents.

SUMMARY OF THE INVENTION

It is therefore to the applicant company's credit, in terms of long and tedious research, that they have proposed using at least one ketose containing 3 to 5 carbon atoms as a substitute for protein-crosslinking agents.

DETAILED DESCRIPTION OF THE INVENTION

Nothing would suggest, in the state of the art, that the use of a ketose containing 3 to 5 carbon atoms may be suitable for tanning proteins and may replace all or some of the usual protein-crosslinking agents, in particular in fields as varied as the tanning of proteins intended for animal feed, the production of film-forming compositions for coverings, coatings or adhesives, and the preparation of biodegradable or renewable protein materials.

Said proteins are then chosen from the group comprising proteins from animal tissues, from milk or from blood, such as in particular casein, gelatin or collagen; proteins from cereals, such as in particular maize, wheat or rice proteins; proteins from high-protein plants, such as in particular pea, alfalfa, lupin, barley, millet or sorghum proteins; proteins from oleaginous plants, such as in particular soybean proteins, for instance soybean cakes, rapeseed or flax proteins, for instance rapeseed cakes, sunflower, groundnut or cotton proteins; proteins from tubers, such as in particular from potato or from manioc.

In the present patent application "proteins from animal tissues" means proteins from tissues of any animals except human being.

According to an advantageous embodiment, the proteins are chosen from the group comprising proteins from cereals, such as in particular maize, wheat or rice proteins; proteins from high-protein plants, such as in particular pea, alfalfa, lupin, barley, millet or sorghum proteins; proteins from oleaginous plants, such as in particular soybean proteins, for instance soybean cakes, rapeseed or flax proteins, for instance rapeseed cakes, sunflower, groundnut or cotton proteins; proteins from tubers, such as in particular from potato or from manioc.

Preferably, the crosslinking agents that are completely or partially substituted with at least one ketose containing 3 to 5 carbon atoms are chosen from the group of mineral tannins, synthetic tannins and aldehyde tannins.

The ketose containing 3 to 5 carbon atoms according to the invention is chosen from the group consisting of dihydroxyacetone, erythrulose, ribulose and xylulose, and is preferably dihydroxyacetone.

The applicant company has found that the reactivity of the ketose containing 3 to 5 carbon atoms used as substitute for crosslinking agents depends on its molecular weight (i.e. its carbon number). The ketoses chosen can thus be classified from the most reactive species (DHA containing 3 carbon atoms) to the least reactive species (xylulose and ribulose containing 5 carbon atoms).

The choice of one or other ketose will therefore depend on the desired degree of crosslinking or on the intended field of application.

According to a first method of use of a ketose containing 3 to 5 carbon atoms, the applicant company has demonstrated that such a ketose can be effectively suitable for and can be recommended for crosslinking proteins intended for animal feed, in particular feed for ruminants or for pets, or in aquaculture.

These proteins may be chosen in particular from the group consisting of animal proteins, cereal proteins, proteins from high-protein plants, proteins from oleaginous plants and proteins from tubers, such as in particular soybean cakes, rapeseed cakes, flax cakes, milk proteins, pea proteins, alfalfa proteins, sunflower, lupin, groundnut, cotton, barley, millet and sorghum proteins, maize, wheat (in particular gluten) and rice proteins, and potato and manioc proteins.

Each of the four ketoses containing 3 to 5 carbon atoms may be used without distinction as agents that substitute for aldehyde tannins.

The applicant company recommends, however, using preferably DHA as a substitute for formol for the tanning of proteins intended for animal feed, in particular feed for ruminants or for pets, or in aquaculture.

The choice of DHA as a substitute for an aldehyde tanning agent is in itself notable, since, to the applicant company's best knowledge, DHA has never been described for the tanning of proteins intended for livestock feed.

In fact, the crosslinking of proteins is here directed towards obtaining resistant proteins, proteins that are less soluble and less bioavailable in the rumen, whereas DHA has, up until now, only been used for its self-bronzing properties.

It is important to note that the present invention is not concerned with the crosslinking properties of DHA, conventionally used in cosmetics, or even sometimes mentioned in pathological processes such as diabetes complications or in protein ageing.

The applicant company has demonstrated that the condensates of resistant proteins obtained by treatment with DHA exhibit, compared with the native proteins from which they are prepared, a modified amino acid content, more particularly in terms of some of their amino acids having a free amine function, such as lysine, arginine, glutamine and asparagine.

The applicant company has found that the amino acids are in the protein in the form of modified products of single, or even double, condensation with the DHA.

DHA preferentially condenses, for example, with lysine and arginine, forming imines. A double condensation can result in crosslinked products.

Moreover, the applicant company has demonstrated that the presence of the hydroxyl group in the alpha-position of the carbonyl function of DHA results in the imine obtained by condensation on a terminal amino acid being able to cyclize with the carboxylic function of this acid so as to form a δ-lactone.

Comparative studies carried out by the applicant company on the modification of proteins by formol have also shown that, among all the amino acids constituting said proteins, it tends to be tyrosine which is modified by the condensation reactions with formol, whereas the lysine and arginine content is not modified.

Without being bound by any theory, it appears that it is this condensation of the ketoses with the free amine function of the amino acids, in particular of the lysine and arginine type (for rapeseed and soybean cakes) and of the glutamine type (for wheat gluten), which makes it possible to explain the resistance shown by the protein condensates in accordance with the invention to the enzyme and microbial attacks undergone by said proteins, for example in the rumen.

In fact, the condensation with these amino acids can prevent the accessibility of degradation enzymes to the proteins by steric hindrance or by local modification of the configuration of said proteins.

The proteins chosen from the group consisting of soybean cakes, rapeseed cakes, flax cakes, milk proteins, pea proteins and wheat (gluten) proteins are particularly suitable for tanning with DHA.

According to a second method of use of the ketoses containing 3 to 5 carbon atoms, the applicant company has shown that it is possible to advantageously substitute the usual agents for crosslinking proteins that are used for preparing film-forming compositions for coverings, coatings or adhesives.

These proteins can then be chosen from the group consisting of proteins from cereals, from tubers, from oleaginous plants, from high-protein plants, from milk, from blood and from animal tissues, preferably casein, gelatin, zein, and high-protein plant isolates.

The applicant company also recommends using preferably DHA. In fact, DHA exhibits notable protein insolubilizing and crosslinking effects, even at ambient temperature, whether neutral or alkaline pH, as will be exemplified hereinafter. As a result, it makes it possible to improve the mechanical properties of protein films, while at the same time adjusting their water resistance.

The applicant company also wishes to emphasize that the crosslinking effect of DHA progresses over time, which characteristic it has demonstrated.

DHA is therefore most particularly suitable for the fields of application targeted, unlike formol, the instantaneous crosslinking nature of which induces too rapid an increase in viscosity.

The slow reactivity of DHA makes it possible, as a result of this, to envisage the use of DHA in the formulation of compositions intended for preparing packaging, protective, coating and surfacing films that are more or less water-soluble.

They may be compositions intended for the detergence field (coating of powders, of fragrances, of enzymes, etc.), the paper surface treatment field (papers, cardboards, etc.), the metallurgy field (sheet metals, etc.), the construction field (coating of cements or of pigments, antigraffiti films, etc.), the agricultural field (coating of seeds, slow-release forms of fertilizer or of plant-protection products, etc.), the veterinary field (coating of vitamins, of trace elements, etc.), the pharmaceutical field (coating or encapsulation of active agents) or the foodstuff field (barrier films, edible films, coating of food products, in particular delicatessen products and confectionery products).

They may also be compositions intended for preparing adhesives requiring very good water resistance and/or excellent adhesivity (mineral or organic particle agglomeration binder, pigment binder, wallpaper adhesive, label adhesive, adhesive for wood, cork, fibrous materials).

The film-forming compositions for coverings, coatings or adhesives obtained according to the invention may comprise, inter alia, various additives such as plasticizers, preserving agents, antioxidants, hydrophobic agents, anticorrosive agents, colorants, fragrances and also active principles.

According to a third method of use of the ketones containing 3 to 5 carbon atoms, the applicant company has demonstrated the possibility of crosslinking proteins intended for the preparation of biodegradable or renewable protein materials, such as plastic films, leathers, textile fibres, gelatin capsules, capsules, or protein food compositions.

The proteins may then be advantageously chosen from the group consisting of proteins from cereals, from tubers, from oleaginous plants, from high-protein plants, from milk, from blood and from animal tissues, preferably collagen, casein, gelatin, zein, and high-protein plant isolates.

They may be compositions intended for the packaging industry (protein films), the photographic industry, the pharmaceutical industry (capsules and gelatin capsules), the rubber industry (additives for tyres), the textile industry (protein fibres) and for plastics technology (moulded or extruded protein objects).

Moreover, the applicant company recommends most particularly using DHA as a substitute for mineral tannins, such as chromium, or for aldehyde tannins, such as formol, for tanning leather. The other ketoses containing 4 and 5 carbon atoms can also be used, although they are less reactive.

To crosslink proteins using a ketose containing 3 to 5 carbon atoms according to the invention, the series of the following steps is carried out, which consists in:
1) bringing the proteins into contact with at least one ketose containing 3 to 5 carbon atoms, at a concentration by dry weight of the ketose of 0.5 to 20%, preferably of 0.5 to 10%, and more preferably of 0.5 to 5%, relative to the dry weight of the crude proteins to be treated,
2) maintaining the contact between the proteins and the ketose for a period of time greater than a few minutes, preferably of between 10 minutes and 60 minutes, preferably for 30 minutes, at a temperature between 20 and 105° C., preferably of between 35 and 105° C.,
3) and recovering the crosslinked proteins thus obtained.

This basic process is valid whatever the nature of the ketose containing 3 to 5 carbon atoms that is chosen, the protein to be treated and the field of application intended.

The applicant company recommends, however, varying the couple time/temperature as a function of the ketose chosen with regard to the intended degree of the crosslinking, as will be described and exemplified hereinafter.

For the crosslinking with DHA of proteins intended for animal feed, the applicant company recommends, in the first step of the process, bringing the proteins and, for example, the DHA into contact at a concentration by dry weight of DHA of 0.5 to 10%, and more preferably of 0.5 to 5%, relative to the dry weight of the crude protein to be treated.

The proteins thus brought into contact are particularly chosen from the group consisting of soybean cakes, rapeseed cakes, flax cakes, pea proteins, soluble gluten, native wheat gluten and lactoserum, as will be exemplified hereinafter.

The temperature for bringing into contact in a mixer or a kneading machine to be selected is then more particularly from 45 to 100° C., for 30 minutes.

The proteins tanned with DHA thus obtained for this field are analysed according to the invention in terms of:
  content of soluble nitrogen/total nitrogen, expressed as %/dry, which reflects the portion of proteins which has not reacted with the DHA, by the method described in the article by R. VERITE and D. DEMARQUILLY entitled *Qualité des matiéres azotées des ailments pour ruminants [Quality of nitrogenous materials in feeds for ruminants]*, in the review *La vache Laitiére [The dairy cow]*, publication INRA 1978, p. 154,
  total amino acid composition, determined by a method developed by the applicant company.

This method for determining the total amino acid composition consists of a 24-hour acid hydrolysis of the proteins and analysis of the released amino acids by high pressure liquid chromatography on ion exchange resin.

For the protein hydrolysis, the weight of sample which should contain 2.8 mg of nitrogen, in 14 ml of 6N HCl, is first of all calculated.

14 ml of 6N HCl are then added to said amount of weight and the mixture is placed under a vacuum for 5 minutes.

After the tube has been closed, it is placed at 115° C. for 24 h.

1 ml of 10 mM Norleucine (sold by the company Sigma), which will serve as an elution control, is then added and the cooled solution is filtered through sintered glass.

The filtrate is recovered in a 250 ml round-bottomed flask and evaporated to dryness at +4° C. The residue is washed with 100 ml of water and evaporated to dryness, and then the washing is repeated twice with 50 ml of water and again dried.

Finally, the dry residue is recovered in 50 ml of lithium Li 280 buffer (sold by the company LC Tech).

The chromatographic analyses by HPLC are carried out on a cation exchange column (column with the reference 0353150 from the company Pickering).

The column is calibrated with 100 µl of a standard amino acid solution (sold by the company Sigma under the reference AAS18) and 20 µl of the Norleucine solution.

100 µl of the hydrolysed protein solution are then injected onto said column, and the amino acids are eluted using a ninhydrin solution at 0.3 ml/min.

The amino acids detected by UV at 570 nm are identified and quantified on the chromatogram obtained.

As will be exemplified hereinafter, the total amino acid compositions are determined on soybean cakes which may or may not have been treated with DHA, comparing them with the total amino acid composition of the said soybean cakes treated with formol.

As regards the possible use of the other ketoses containing 4 or 5 carbon atoms as substituents for tanning agents for proteins intended for this same application, it is illustrated by the determination of the reactivity of xylulose and of ribulose on lysine, at a temperature of 80° C., as will also be exemplified hereinafter.

For the crosslinking with DHA of proteins intended for the preparation of films, in particular for the crosslinking of casein, of gelatin or of high-protein plant isolates, the applicant company recommends, in the first step of the process, bringing the protein and the DHA into contact at a concentration by dry weight of DHA of 1 to 10%, and more preferably of 1 to 5%, relative to the dry weight of the crude protein to be treated.

The bringing into contact is carried out at ambient temperature for a few minutes, and the tanned proteins thus obtained are analysed in terms of adhesive viscosity, of insolubilizing effect, and of properties of the films obtained (in particular of mechanical resistance), as will be exemplified hereinafter.

For the preparation of leathers tanned with DHA, the series of steps 1 to 3 described above is also suitable.

Other characteristics and advantages of the invention will emerge on reading the nonlimiting examples described below.

Example 1

6 condensates of proteins tanned with dihydroxyacetone are produced using soybean cakes (sold by the company Uneal), rapeseed cakes (produced by Moulins Delsalle), pea proteins (sold by the company Cosucra under the trademark PISANE® HD), soluble gluten (sold by the applicant company under the trademark VITEN® CWS), native wheat gluten (sold by the applicant company under the trademark VITEN®) and lactoserum proteins (sold by the company Armor Proteines under the trademark PROTARMOR® 865).

The DHA can be used pure (sold by the company Sigma) or used directly in the form of a fermentation supernatant from microorganisms producing it from glycerol coproduct of the diester ("technical" DHA).

If pure DHA is chosen, said DHA is, firstly, diluted in a volume of water such that the final DHA/protein ratio corresponds to the desired value.

It is generally a solution of 10 to 25% of solids.

The DNA solution is left for 30 minutes in order to stabilize it in the form of monomers. The pH is adjusted to 6 with 0.1N sodium hydroxide.

The proteins are preheated at 100° C. in a kneading machine for 30 minutes, the DHA is added, the mixture is homogenized, and the actual bringing into contact of the proteins with the DHA is carried out at a temperature of 95 to 100° C. for a further 30 minutes.

The results in Table I make it possible to estimate the insolubilizing properties of the DHA, by determining the soluble nitrogen/total nitrogen ratios for the 6 protein condensates after tanning with DHA at doses of 1, 2.5 and 5% on a dry weight/dry weight of treated proteins basis.

TABLE I

|  | Soybean | Rapeseed | Pea | Viten ® CWS | Viten ® | Lactoserum |
|---|---|---|---|---|---|---|
| Start | 18 | 21 | 22 | 67 | 8.4 | 98 |
| 1% DHA | 5 | 14 | 8 | 52 | 3 | 24 |
| 2.5% DHA | 3 | 5 | 3 | 53 | 1 | 16 |
| 5% DHA | 3 | 6 | 5 | Nd | 1 | 10 |
| 1% formaldehyde | 5 | Nd | Nd | Nd | Nd | Nd |

The higher the dose of DHA, the lower the soluble nitrogen/total nitrogen ratio, but a significant effect is already obtained at the dose of 1%.

The comparative trial for tanning of soybean cakes with formol shows that the protein-insolubilizing effect realized by treatment with DHA at the dose of 1% is equivalent to that obtained with formol at the dose of 1%.

DHA is therefore a substitute for formol that is entirely effective for tanning proteins intended for ruminant feed, whatever their nature might be.

Parallel trials were carried out on rapeseed cakes and soybean cakes, in order to study the effect of temperature and of contact time.

It is thus shown that the reaction takes place readily, even at ambient temperature, with a significant result within the first 10 minutes of contact.

It was also noted that soybean is more reactive than rapeseed.

Table II below gives the amino acid results determined on native proteins (rapeseed and soybean taken as an example), and then on proteins treated with 1% of DHA.

TABLE II

| Amino acids | Soybean | | Rapeseed | | Soybean | |
|---|---|---|---|---|---|---|
|  | Native | +DHA | Native | +DHA | Native | +formol |
| Asp | 11.8 | 11.9 | 8 | 8.2 | 11.8 | 12 |
| Thr | 4.2 | 4.1 | 5.1 | 5.2 | 3.95 | 3.8 |
| Ser | 5.3 | 5.4 | 4.8 | 5.2 | 5.3 | 4.9 |
| Glu | 19.9 | 20.2 | 20.1 | 20.5 | 19.9 | 20.2 |
| Gly | 4.4 | 4.6 | 5.7 | 5.8 | 4.4 | 4.45 |
| Ala | 4.4 | 4.4 | 4.8 | 5.1 | 4.4 | 4.45 |
| Val | 5.1 | 5.1 | 5.7 | 6.3 | 5.1 | 5.3 |
| Ile | 4.8 | 4.9 | 4.5 | 4.5 | 4.85 | 5.1 |
| Leu | 8.1 | 8.3 | 8 | 8.3 | 8.1 | 8.2 |
| Tyr | 3.9 | 4.1 | 3.4 | 3.5 | 4 | 3.5 |
| Phe | 5.3 | 5.4 | 4.5 | 4.5 | 5.3 | 5.3 |
| Lys | 6.5 | 5.8 | 6.4 | 5.6 | 6.5 | 6.4 |
| His | 2.7 | 2.7 | 3.1 | 3.1 | 2.8 | 2.7 |
| Arg | 8.1 | 7.3 | 8.3 | 6.9 | 8.1 | 8.2 |
| Pro | 5.5 | 5.8 | 7.6 | 7.3 | 5.5 | 5.5 |
| Total AA | 100 | 100 | 100 | 100 | 100 | 100 |

The tanning of soybean cake proteins and of rapeseed cake proteins with 1% of DHA results in a decrease in the lysine content of the order of 10.8% (in the case of soybean) and of the order of 12.7% (in the case of rapeseed), and a decrease in the arginine content of the order of 9.9% (in the case of soybean) and of the order of 16.9% (in the case of rapeseed), indicating, by the same token, that the reactions condensing these proteins with DHA target more particularly the free amine functions of these two amino acids constituting the peptide chains.

By comparison, the reactions condensing formol with the soybean proteins mainly occur with the tyrosine residues of the peptide chains. It thus appears that DHA, just like formol, combines readily with the proteins intended for ruminant feed, with a reactivity equivalent to that of formol, the toxicity of course being less.

Example 2

The soybean cakes of Example 1, treated or not treated with DHA, are digested with a combination of an α-amylase (Solvay Amylase—LF60 sold by the company Solvay Enzymes), a cellulase (Spezyme CP sold by the company Genencor) and a pepsin (Pepsine P-7000 sold by the company Sigma), in order to determine the degree of resistance of the proteins thus obtained.

This in vitro test makes it possible to evaluate the effectiveness of the tanning reaction and the protein availability after by-pass of the rumen. This pepsin digestion also makes it possible to simulate the pH and the enzyme degradation in the stomach.

For this evaluation, two series of digestion are therefore carried out in parallel:
  a first series with two enzymes (AC protocol), i.e. α-amylase and cellulase, in order to estimate the effectiveness of the tanning reaction (proteins resistant to the enzymes of the rumen),
  a second series with the three enzymes (ACP protocol), i.e. α-amylase, cellulase and pepsin (the pepsin digestion reflecting the digestibility of the tanned proteins after passage in the rumen, here in the stomach).

The enzyme digestion of the tanned or non-tanned proteins is carried out according to the following protocol:
1) 2.5 g of dry product are weighed out,
2) 25 ml of 0.075N HCl at pH 4 are added,
3) the mixture is stirred for 1 h at ambient temperature (the pH is adjusted to 4 if necessary),
4) 200 of α-amylase (at 60 000 MWU/ml·min) and 200 µl (at 90 GCU/ml) of cellulase are added, 5) the mixture is left for 3 hours, with stirring, in a waterbath at 40° C.,
6) 25 ml of 0.075N HCl at pH 1.2 are added,
7) the mixture is stirred and the pH is verified (the pH is adjusted to 1.5 if necessary),
8) in this step, the pepsin (in the case of the ACP protocol) is added in a proportion of 500 µl of pepsin at a concentration of 5 g/l, prepared extemporaneously,
9) the mixture is then placed in a waterbath at 40° C. and stirred continually for 20 h,
10) the digestion material is collected and allowed to separate by settling out, and two times 15 ml of supernatant are removed and centrifugation is performed at 4000 rpm for 20 min,
11) the supernatant is recovered and can be frozen for storage.

The degree of hydrolysis of the proteins is determined by a method of assaying the primary amino groups of the proteins treated with trinitrobenzenesulphonic acid (TNBS), This method consists in:
adding 250 µl of 5% SDS (sodium dodecyl sulphate) to 250 µl of sample to be analysed,
leaving the mixture for 30 min at 0.50° C.,
adding 2 ml of phosphate buffer at pH 8.2,
adding 2 ml of 1% TNBS,
placing the mixture in a waterbath at 50° C. for 1 h,
adding 4 ml of 0.1M HCl,
leaving the mixture at ambient temperature for 30 min,
removing 250 µl and reading on a spectrophotometer at 340 nm.

A standard range is prepared with a 10 mM leucine solution.

The results of enzyme digestion on the samples can be expressed as concentration of leucine equivalent (LE) expressed as mMol/l or as % (decrease in the TNBS response relative to the native protein).

Table III below gives the digestibility values obtained for the soybean cakes treated with varying doses of DHA (1 and 2.5%) according to the implementation described in Example 1.

TABLE III

| Concentration of DHA | No enzyme treatment | | AC protocol | | ACP protocol | |
|---|---|---|---|---|---|---|
| | LE | % | LE | % | LE | % |
| 0 | 2.40 | 100 | 3.17 | 100 | 17.03 | 100 |
| 1% | 1.49 | 62.2 | 1.97 | 62.0 | 14.61 | 85.8 |
| 2.5% | 0.53 | 22.1 | 0.68 | 21.4 | 9.79 | 57.5 |

It is noted that, the higher the dose of DHA, the less sensitive the cakes are to digestion with α-amylase and cellulase (thus reflecting good protection in the rumen), while at the same time allowing good sensitivity to pepsin, which reflects a satisfactory bioavailability (after bypass of the rumen).

At the dose of 1% of DHA, the tanned proteins are virtually undigested (the % response value goes from 62.2 to 62%). However, the addition of pepsin renders more than 85% of said proteins available.

However, it should be noted that the dose of 2.5% of DHA has a considerable protective effect, since, after treatment with pepsin, only 57.5% of the proteins are available.

The dose of 1% of DHA should therefore be selected for the tanning of proteins intended for ruminant feed.

Equivalent results are obtained with the rapeseed cakes, as indicated in Table IV below.

TABLE IV

| Concentration of DHA | No enzyme treatment | | AC protocol | | ACP protocol | |
|---|---|---|---|---|---|---|
| | LE | % | LE | % | LE | % |
| 0 | 1.60 | 100 | 2.13 | 100 | 8.40 | 100 |
| 1% | 1.32 | 82.8 | 1.87 | 87.7 | 7.36 | 87.6 |
| 2.5% | 0.81 | 50.9 | 1.16 | 54.4 | 5.16 | 61.4 |

It is thus confirmed that the process for tanning with DHA is more effective for the soybean cakes than for the rapeseed cakes (cf. one of the conclusions of Example 1).

Example 3

In this instance, the soybean cakes of Example 1, treated or not treated with DHA, are digested with the combination of enzymes of Example 2, to which trypsin is added (trypsin T 8003 derived from bovine pancreas, sold by the company Sigma).

This in vitro test with trypsin makes it possible to simulate the enzyme attacks of the small intestine on cakes treated or not treated with DHA, after they have passed through the stomach.

For this evaluation, three series of digestion are therefore carried out in parallel:
a first series with two enzymes (AC protocol), i.e. α-amylase and cellulase, in order to estimate the effectiveness of the tanning reaction (proteins resistant to the enzymes of the rumen),
a second series with the three enzymes (ACP protocol), i.e. α-amylase, cellulase and pepsin,
a third series with the four enzymes (ACPT protocol), i.e. α-amylase, cellulose, pepsin and trypsin.

The enzyme digestion of the tanned or non-tanned proteins is carried out according to the protocol of Example 2 up until step No. 8.

Step No. 9 and the subsequent steps are then:
9) the mixture is placed in a waterbath at 40° C. and stirred continually for 18 h,
10) the mixture is adjusted to pH 7.5 with 4N sodium hydroxide,
11) 500 µl of trypsin at 5 g/l (specific activity of 10 000 U/mg of proteins) are added,
12) the mixture is stirred for 6 hours,
13) the digested material is collected and allowed to separate by settling out, two times 15 ml of supernatant are removed and centrifugation is carried out at 4000 rpm for 20 min,
14) the supernatant is recovered and can be frozen for storage.

The degree of hydrolysis of the proteins is also determined by the method of assaying the primary amino groups of the proteins treated with trinitrobenzene-sulphonic acid (TNBS) of Example 2. The results of enzyme digestion on the samples are expressed as concentration of leucine equivalent (LE) expressed as mMol/l.

Table V below gives the digestibility values obtained for the soybean cakes treated with varying doses of DHA (1 to 10%) according to the implementation described in Example 1.

TABLE V

| Concentration of DHA | No enzyme treatment | AC protocol | ACP protocol | ACPT protocol |
|---|---|---|---|---|
| 0 | 2.78 | 3.08 | 14.42 | 30.45 |
| 1% | 1.48 | 1.84 | 13.37 | 25.01 |
| 2, 5% | 0.46 | 0.80 | 9.10 | 16.22 |
| 5% | 0.48 | 0.71 | 8.05 | 14.08 |
| 10% | 0 | 0.09 | 6.61 | 9.61 |

Equivalent results are obtained with the rapeseed cakes, as indicated in Table VI below.

TABLE VI

| Concentration of DHA | No enzyme treatment | AC protocol | ACP protocol | ACPT protocol |
|---|---|---|---|---|
| 0 | 1.78 | 2.13 | 7.61 | 16.06 |
| 1% | 1.43 | 1.80 | 6.52 | 12.83 |
| 2, 5% | 0.90 | 1.26 | 5.12 | 9.25 |
| 5% | 0.56 | 0.89 | 4.19 | 7.10 |
| 10% | 0.23 | 0.40 | 3.61 | 5.21 |

It is noted that the amylase and cellulase digestion (AC protocol) has little effect on the freeing of the amine functions of the rapeseed and soybean proteins. This digestion does not therefore make it possible to restore the proteins tanned with DHA. These proteins will therefore remain inaccessible in the rumen (cellulase activity is important in the rumen).

The pepsin and trypsin digestions of the proteins effectively free additional amine functions. The reaction consisting of DHA-tanning of soybean and rapeseed proteins is therefore a reversible reaction that ensures bioavailability of said proteins in the stomach and the small intestine.

As had been noted in Example 2, the soybean proteins appear to be more readily digested by the enzyme complexes used, than the rapeseed proteins.

Finally, the results obtained show that, above 5% tanning with DHA, the effectiveness of the reaction is no longer as great.

The compromise between tanning and pepsin and trypsin digestion lies between 1 and 2.5% of DHA.

Example 4

The crosslinking effect of DHA with respect to casein is evaluated in the following way:

Stock casein adhesives are first of all prepared and said adhesives are then used for preparing films by casting.
1) Process for Preparing Casein Adhesives An aqueous solution containing 15% of casein H solids, sold by the company SVPC, is prepared.

Complete solubilization is obtained by adjusting the pH to 9 by adding sodium hydroxide at 200 g/l, heating to 50° C. and stirring at 1000 rpm for 20 min.

This solution is cooled to ambient temperature and DHA is incorporated, or is not incorporated, in the form of a solution containing 50% of solids, adjusting the pH to 7.5 or to 9 (97%-pure DHA, as sold by the company Sigma).

The results of the Brookfield viscosity measurements, as a function of pH, on the casein adhesives that have been treated with DHA (5% of a 50% solution, i.e. 2.5% by dry weight relative to the crude casein), or not treated, are given in the tables below.

Table VII shows the evolution of the viscosity of the adhesives as a function of the pH, without DHA.

Table VIII shows the evolution of the viscosity of the adhesives at pH 7.5 or at pH 9 with 2.5% of DHA.

TABLE VII

| pH | 7 | 7.5 | 8 | 9 |
|---|---|---|---|---|
| Brookfield viscosity at 40° C. (mPa · s) | 6000 | 4500 | 5200 | 5000 |

TABLE VIII

| | Time | | | | | |
|---|---|---|---|---|---|---|
| | 15 min | 30 min | 1 h | 2 h | 3 h | 12 h |
| Brookfield viscosity at 40° C. (mPa · s) measured at pH 7.5 | 6500 | Nd* | Nd | Nd | 25 000 | Nd |
| Brookfield viscosity at 40° C. (mPa · s) measured at pH 9 | 6500 | 7500 | 13 000 | 150 000 | Nd | >200 000 |

*Not determined

The addition of 5% of DHA at 50% of solids (2.5% dry weight/casein) results, at a pH of 9, in a very clear but gradual increase in the viscosity of the adhesive.

At pH 7.5, the increase in viscosity is slower, but notable.

By comparison, the addition of an equivalent amount of formol resulted in the adhesive setting solid virtually instantaneously.

These trials demonstrate an effect of gradual crosslinking of the casein by DHA over time, at ambient temperature, this taking place more rapidly at pH 9 than at pH 7.5.
2) Process for Preparing the Casein Films Obtained by Casting The casein films are prepared by casting (spreading on a support) using a Sheen 1102 device set at a thickness of 700 μm, and then slow drying over 24 h at 20° C. and at 65% residual humidity.

The characteristics of the films obtained are given in Table IX below.

TABLE IX

| | Appearance of the films without DHA | Appearance of the films with DHA |
|---|---|---|
| pH 7.5 | Films very fragile, soluble in water in a few minutes | Films fragmented and fragile, insoluble in water |
| pH 9 | Films very fragile, soluble in water in a few minutes | Resistant and flexible, insoluble in water |

At pH 7.5 or 9, with 2.5% of DHA by dry weight/casein, the water resistance of the films is particularly good, since the films remain intact in water after more than one week, in the presence of a biocidal agent. The addition of DHA thus confers excellent water-resistance while at the same time improving the mechanical properties of the films.

In this respect, it should be mentioned that it is impossible to produce such films with the addition of formol, due to the fact that there is too great an instantaneous increase in the viscosity of the adhesives.

Example 5

The insolubilizing effect of DHA on casein is estimated by means of a method for determining the content of soluble materials, developed by the applicant company.

It consists in introducing 200 ml of demineralized water into a 400 ml beaker, and in placing therein, with magnetic stirring, exactly 5 g of the sample to be analysed.

The mixture is homogenized for 15 minutes by means of the magnetic stirrer and is then centrifuged for 15 minutes at 5500 rpm. 25 ml of the supernatant liquid are removed and are introduced into a tared crystallizer.

Said crystallizer is placed in a microwave oven for 10 minutes at 600 watts and 5 minutes at 900 watts until the sample is completely dehydrated. It is then placed in a desiccator in order to cool it to ambient temperature.

The crystallizer is re-weighed and the mass m of residue is recorded.

The content of soluble materials (Csm), expressed as percentage by weight of the product, is given by the following formula: Csm=(m×200×100)/(25×5).

Table X below gives the results of solubilities of casein films prepared by casting at ambient temperature, using a solution of casein at 15% of solids, according to the conditions given in Example 3.

TABLE X

| Dose of DHA by dry weight/casein (%) | Csm (%) |
|---|---|
| 0 | 86 |
| 0.5 | 86 |
| 1.5 | 13.9 |
| 2.5 | 6.7 |

The aqueous solubility of the casein films is decreased through using DHA in an amount greater than 0.5% by dry weight/casein. The dose of 2.5% is preferred for obtaining a film which is virtually water-insoluble.

Example 6

Trials consisting in coating tablets of mannitol (sold by the applicant company under the trademark PEARLITOL® DC) with aqueous solutions of pea protein isolates (sold under the trademark PISANE® HD by the company Cosucra) are carried out.

Three aqueous solutions of proteins having a viscosity in the region of 500 mPa·s at ambient temperature (measured on a Brookfield viscosimeter) are prepared:
 the first, by dispersing 12 g dry weight of PISANE® HD per 100 g of water at 50° C. and adjusting the final pH to 9.7 (solution A),
 the second, by dispersing 12 g dry weight of PISANE® HD and 1.2 g of aqueous solution of DHA at 50% of solids, per 100 g of water at 50° C. and adjusting the final pH to 9.7 (solution B),
 the third, by dispersing 12 g dry weight of PISANE® HD, 1.2 g of aqueous solution of DHA at 50% of solids and 2.4 g of glycerol, per 100 g of water at 50° C. and adjusting the final pH to 9.7 (solution C).

Each of these solutions is used for coating, by spraying, 200 g of mannitol tablets placed in an Erweka coating pan, revolving at a rate of 30 rpm, into which pulsed dry air at a temperature of 65° C. is constantly introduced.

The flow rate of the solution is such that the coating is carried out in 45 minutes. The dry final protein coat then represents approximately 9% of the initial mass of the tablets.

The rate of escape of mannitol through the protein coating is evaluated by placing 7.5 g of tablets in 45.5 g of demineralized water, with mechanical stirring, and measuring the solids (expressed as brix) that appear in the water over time.

The results obtained are given in Table XI below.

TABLE XI

| Time (min) | Tablets of Pearlitol ® DC not coated | Tablets of Pearlitol ® DC coated with solution A | Tablets of Pearlitol ® DC coated with solution B | Tablets of Pearlitol ® DC coated with solution C |
|---|---|---|---|---|
| 1 | 2.4 | 0.4 | 0.2 | 0.0 |
| 2 | 5.0 | 1.4 | 0.8 | 0.1 |
| 5 | 9.0 | 6.0 | 3.0 | 0.4 |
| 10 | 13.4 | 9.8 | 5.4 | 1.0 |
| 15 | 14.2 | 12.0 | 7.0 | 1.6 |
| 25 | 14.5 | 13.6 | 9.0 | 2.9 |
| 45 | 14.5 | 13.8 | 10.4 | 4.8 |
| 120 | 14.5 | 14.0 | 12.0 | 9.2 |
| 240 | 14.5 | 14.5 | 14.0 | 14.0 |

It is noted that the escape of mannitol through the dissolving of the tablets is similar between the uncoated tablets and the tablets coated with the solution of PISANE® HD pea proteins without DHA.

On the other hand, the tablets coated with solution B or solution C comprising DHA clearly show less escape of mannitol, in particular when the coating contains DHA in combination with glycerol.

These solutions B and C may be suitable for preparing a coating for food products, for plant-protection products (based on pesticides, insecticides, herbicides, fungicides etc.), for veterinary products, for pharmaceutical products or else for industrial products (based on enzymes, on colorants, on biocides, etc.) in order to obtain delayed-release forms, formulations protected against ageing (UV, oxidation, temperature, hydrolysis, etc.) or compositions having an improved organoleptic aspect (brilliance, colour, etc.).

Example 7

The "tanning" capacities of ribulose and of xylulose are estimated by monitoring the reactivity of these two ketoses with one of the most reactive amino acids of the proteins intended for ruminant feed: lysine, in comparison with glutamic acid.

The tanning action is normally obtained by binding of the aldehyde with the ε-amino group of lysine. A Schiff's base which gives a readily detectable yellow colour is then created.

The coloration of the reaction medium over time is measured (ICUMSA coloration measurement) in the following way:
 10 ml of each 1M stock solution of ribulose, of xylulose, of lysine and of glutamic acid in demineralized water, at a pH of 6, are prepared,
 5 ml of the amino acid and 5 ml of the ketose to be tested are added to a test tube,
 the mixture obtained is homogenized and is placed in an oil bath at 80° C. in order to react,
 the reaction is stopped at +4° C.

Table XII below gives the kinetics of condensation of the ribulose and of the xylulose with lysine and glutamic acid, the results being expressed by the absorbance at 420 nm, reflecting the coloration obtained.

As control products, comparative trials of condensation of lysine with fructose, and trials of condensation of ribulose and of xylulose with a control amino acid, glutamic acid, are carried out in parallel.

TABLE XII

|  |  | Time (min) | | | | |
| --- | --- | --- | --- | --- | --- | --- |
|  |  | 0 | 15 | 30 | 60 | 120 |
| Ribulose | Glu | 0.033 | 0.170 | 0.495 | 1.252 | 10.535 |
|  | Lys | 0.086 | 1.743 | 4.653 | 15.899 | 38.658 |
| Xylulose | Glu | 0.096 | 0.666 | 0.922 | 1.930 | 3.021 |
|  | Lys | 0.145 | 2.787 | 4.324 | 8.399 | 17.541 |
| Fructose | Glu | 0.008 | 0.021 | 0.044 | 0.112 | 0.280 |
|  | Lys | 0.012 | 0.019 | 0.030 | 0.120 | 0.519 |

It appears that ribulose and xylulose are also good tanning agents for the protection of proteins.

Moreover, it should be noted that the kinetics of complexation with the free amino acid are quite rapid, since first condensation products appear within the first 15 minutes of the reaction.

It also appears that fructose is a poor tanning agent and is entirely unsuitable for the fields of application targeted by the present invention.

The ketoses containing 5 carbon atoms are therefore sufficiently reactive to envisage effective tanning of proteins intended for animal feed, or for the preparation of film-forming compositions, or else of biodegradable or renewable materials.

Example 8

Trials consisting in producing feed for shrimp are carried out, with tanning of proteins using xylulose or DHA instead of a conventional urea-formol (Maxibond compound sold by the company Agresearch Inc., Joliet, Ill., USA).

Table XIII below gives the content of ingredients (expressed as % of weight/weight) of the 5 feeds thus prepared (percentage calculated for a total weight of ingredients of 3 kg).

TABLE XIII

| Nature of the ingredients of the feeds | Feed No. 1 | Feed No. 2 | Feed No. 3 | Feed No. 4 | Feed No. 5 |
| --- | --- | --- | --- | --- | --- |
| Wheat flour | 29.6 | 26.4 | 26.4 | 26.4 | 26.4 |
| Gluten |  | 3.2 | 3.2 | 3.2 | 3.2 |
| Fish meal | 33.6 | 33.6 | 33.6 | 33.6 | 35.2 |
| Ground soybean cakes | 12 | 12 | 12 | 12 | 12 |
| Soybean oil | 2.4 | 2.4 | 2.4 | 2.4 | 2.4 |
| Lecithin | 0.8 | 0.8 | 0.8 | 0.8 | 0.8 |
| Maxibond | 1.6 | 1.6 |  |  |  |
| Xylulose (58% solids) |  |  | 1.6 |  |  |
| DHA |  |  |  | 1.6 |  |
| Water | 20 | 20 | 20 | 20 | 20 |

It is thus noted that feed No. 2 is tanned with Maxibond, feed No. 3 is tanned with xylulose, feed No. 4 is tanned with DHA and feed No. 5 is a non-tanned control feed.

Feed No. 1 is a control tanned with Maxibond which does not contain any gluten.

The feed is prepared according to the following procedure:
1) the ingredients in powdered form (i.e. wheat flour, gluten, fish meal, ground soybean cakes and Maxibond according to the formulae) are mixed with a Hobart planetary mixer for 3 min at speed 1,
2) the soybean oil and the lecithin are added,
3) the mixture is homogenized with the Hobart planetary mixer for 3 min at speed 1,
4) the mixture is placed in an oven at 95° C. until the temperature of the mixture reaches 80° C.,
5) the xylulose or the DHA is dissolved in water at 80° C.,
6) the xylulose or the DHA thus solubilized is added in the desired proportions,
7) the mixture is mixed with the Hobart mixer for 5 min at speed 1,
8) the mixture thus obtained is textured, under cold conditions, on a Buhler single-screw extruder under the conditions given in Table XIV below,
9) the extruded materials are then dried in an oven at 80° C. for approximately 15 hours.

TABLE XIV

|  | Feed No. 1 | Feed No. 2 | Feed No. 3 | Feed No. 4 | Feed No. 5 |
| --- | --- | --- | --- | --- | --- |
| Water content of the starting mixture (%) | 12.42 | 11.71 | 11.41 | 11.52 | 11.24 |
| Water content after having been placed in the oven (%) | 8.54 | 9.59 | Nd* | 7.92 | Nd |
| Water content before extrusion (%) | 23.39 | 25.77 | 24.8 | 25.17 | 23.84 |

The characteristics of the compositions and then of the extruded materials thus produced are given in Table XV below.

TABLE XV

|  | Feed No. 1 | Feed No. 2 | Feed No. 3 | Feed No. 4 | Feed No. 5 |
| --- | --- | --- | --- | --- | --- |
| Water content after extrusion (%) | 20.66 | 22.53 | 22.35 | 23.49 | 23.02 |
| Final water content (%) | 6.46 | 7.43 | 6.22 | 7.71 | 7.52 |
| Disintegration time in water with a 3.5% salt content (min) | >120 | >120 | >120 | >120 | <10 |

*Nd = not determined

As was expected, the non-tanned feed 5 is not stable; it disintegrates rapidly in seawater.

The feeds tanned with xylulose or with DHA show, on the other hand, notable properties of stability, comparable with the feeds tanned with urea-formol.

The applicant company observed, moreover, that the water resistances of feeds No. 1 and No. 4 are equivalent.

It can be deduced therefrom that DHA or xylulose can substitute advantageously for the more toxic tanning agents such as urea-formol for this particular application in aquaculture.

The invention claimed is:
1. A process for crosslinking proteins, comprising:
crosslinking a protein by contacting a crosslinking agent with the protein at dry weight concentration of 0.5 to 20% of the crosslinking agent relative to the protein and maintaining contact between the crosslinking agent and the protein at a temperature between 20 and 105° C. for a period of time between greater than a few minutes and 60 minutes, wherein the period time is sufficient to obtain crosslinked water insoluble proteins; and
recovering the crosslinked water insoluble protein, wherein, the crosslinking agent is a ketose selected from the group consisting of erythrulose, ribulose and xylulose, and the protein is selected from the group consisting of proteins from cereals, proteins from high-protein plants, proteins from oleaginous plants, and proteins from tubers.

2. The process according to claim 1, wherein the protein is selected from the group consisting of soybean cakes, rapeseed cakes, flax cakes, pea proteins, and wheat proteins.

3. The process according to claim 1, wherein the protein is selected from the groups consisting of maize proteins, wheat proteins, rice proteins; proteins from high-protein plants, pea proteins, alfalfa proteins, lupin proteins, barley proteins, millet proteins, sorghum proteins, proteins from oleaginous plants, soybean proteins, soybean cakes, rapeseed proteins, flax proteins rapeseed cakes, sunflower proteins, groundnut proteins, cotton proteins, and proteins from tubers, potato proteins, and manioc proteins.

4. A water insoluble protein crosslinked with ketoses, wherein said protein is obtained by the process according to claim 1.

5. The process according to claim 1, further comprising introducing the crosslinked water insoluble protein into a feed composition.

6. The process according to claim 1, wherein the protein is a high-protein plant isolate.

* * * * *